(12) United States Patent
Reillo et al.

(10) Patent No.: US 10,084,044 B2
(45) Date of Patent: *Sep. 25, 2018

(54) FOOD AND BEVERAGE COMPOSITIONS INFUSED WITH LIPOPHILIC ACTIVE AGENTS AND METHODS OF USE THEREOF

(71) Applicant: PoViva Tea, LLC, Reno, NV (US)

(72) Inventors: Michelle Reillo, Saint Augustine, FL (US); Marian E. Washington, Saint Augustine, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/952,205

(22) Filed: Apr. 12, 2018

(65) Prior Publication Data

US 2018/0233559 A1 Aug. 16, 2018

Related U.S. Application Data

(60) Continuation of application No. 15/808,889, filed on Nov. 10, 2017, now Pat. No. 9,972,680, which is a
(Continued)

(51) Int. Cl.
*A61K 31/60* (2006.01)
*H01L 29/06* (2006.01)
(Continued)

(52) U.S. Cl.
CPC .......... *H01L 29/0673* (2013.01); *B82Y 10/00* (2013.01); *H01L 21/02381* (2013.01); *H01L 21/02461* (2013.01); *H01L 21/02532* (2013.01); *H01L 21/02603* (2013.01); *H01L 21/823807* (2013.01); *H01L 29/42376* (2013.01); *H01L 29/42392* (2013.01); *H01L 29/66439* (2013.01);
(Continued)

(58) Field of Classification Search
CPC ....... H01L 21/02381; H01L 21/823807; H01L 21/02461; H01L 21/02603; H01L 21/02532; H01L 29/0673; H01L 29/66439; H01L 29/785; H01L 29/66795; H01L 29/66545; H01L 29/42376; B82Y 10/00
USPC ........................................................ 514/165
See application file for complete search history.

(56) References Cited

U.S. PATENT DOCUMENTS 9,972,680 B2 * 5/2018 Reillo ................. H01L 29/0673
2008/0008781 A1 1/2008 Sweeney et al.
(Continued)

FOREIGN PATENT DOCUMENTS

DE 19746830 C1 8/1999
WO 2013138906 A1 9/2013

OTHER PUBLICATIONS

EP Application No. 15806768.6 Extended European Search Report and Written Opinion, dated Nov. 24, 2017.

*Primary Examiner* — Taylor V Oh
(74) *Attorney, Agent, or Firm* — Edward R. Ergenzinger

(57) ABSTRACT

Aspects described herein relate to food and beverage compositions infused with lipophilic active agents and methods of use for the treatment of a variety of disorders. More particularly, aspects described herein relate to food and beverage compositions infused with lipophilic active agents such as cannabinoids, nicotine, nonsteroidal anti-inflammatories (NSAIDs), and vitamins, that provide enhanced bioavailability of the lipophilic active agents in a subject, and that mask unpleasant tastes of lipophilic active agents.

18 Claims, 6 Drawing Sheets

Related U.S. Application Data division of application No. 15/225,802, filed on Aug. 1, 2016, now Pat. No. 9,974,739, which is a continuation of application No. 14/735,844, filed on Jun. 10, 2015, now Pat. No. 9,474,725.

(60) Provisional application No. 62/161,324, filed on May 14, 2015, provisional application No. 62/153,835, filed on Apr. 28, 2015, provisional application No. 62/037,706, filed on Aug. 15, 2014, provisional application No. 62/010,601, filed on Jun. 11, 2014.

(51) Int. Cl.
| | | |
|---|---|---|
| *H01L 21/8238* | (2006.01) | |
| *B82Y 10/00* | (2011.01) | |
| *H01L 29/423* | (2006.01) | |
| *H01L 21/02* | (2006.01) | |
| *H01L 29/66* | (2006.01) | |
| *H01L 29/78* | (2006.01) | |
| *H01L 29/775* | (2006.01) | |
| *H01L 27/092* | (2006.01) | |

(52) U.S. Cl.
CPC .. *H01L 29/66545* (2013.01); *H01L 29/66795* (2013.01); *H01L 29/775* (2013.01); *H01L 29/785* (2013.01); *H01L 27/092* (2013.01)

(56) References Cited

U.S. PATENT DOCUMENTS

| | | |
|---|---|---|
| 2008/0254153 A1 | 10/2008 | Wang et al. |
| 2012/0043242 A1 | 2/2012 | Hospodor |
| 2013/0089600 A1 | 4/2013 | Winnicki |
| 2013/0296415 A1 | 11/2013 | Goskonda et al. |

* cited by examiner

FOOD AND BEVERAGE COMPOSITIONS INFUSED WITH LIPOPHILIC ACTIVE AGENTS AND METHODS OF USE THEREOF

CROSS-REFERENCE TO RELATED APPLICATIONS

This application is a continuation of U.S. application Ser. No. 15/808,889, filed Nov. 10, 2017; which was a divisional of U.S. application Ser. No. 15/225,802 filed on Aug. 1, 2016; which claims the benefit of U.S. application Ser. No. 14/735,844 filed on Jun. 10, 2015; which claims the benefit of U.S. Provisional Application No. 62/010,601, filed Jun. 11, 2014, U.S. Provisional Application No. 62/037,706, filed Aug. 15, 2014, U.S. Provisional Patent Application No. 62/153,835 filed Apr. 28, 2015, and U.S. Provisional Patent Application No. 62/161,324 filed May 14, 2015; each of which are incorporated herein by reference in their entireties.

TECHNICAL FIELD

Aspects described herein relate to food and beverage compositions infused with lipophilic active agents and methods of use for the treatment of a variety of disorders. More particularly, aspects described herein relate to food and beverage compositions infused with lipophilic active agents such as cannabinoids, nicotine, nonsteroidal anti-inflammatories (NSAIDs), and vitamins, that provide enhanced bioavailability of the lipophilic active agents in a subject, and that mask unpleasant tastes of lipophilic active agents.

BACKGROUND

Many therapeutic agents are highly lipophilic, meaning that they are soluble in lipids and some organic solvents while being substantially insoluble or only sparsely soluble in water. The poor water-solubility of these lipophilic agents often results in major difficulties in formulation. When administered in the form of an oil solution or some kind of water and/or oil suspension or emulsion, lipophilic compounds usually show poor bioavailability.

Various approaches to overcoming this limitation are known in the prior art. One such approach consists of dissolving a lipophilic compound in a water-miscible organic solvent such as ethanol or propylene glycol. However, when the resulting solution is admixed with blood or gastrointestinal fluids, the lipophilic compound usually precipitates as a solid or liquid emulsion, which results in a low bioavailability. Furthermore, for many lipophilic compounds no water-miscible organic solvents exist.

Another approach involves physico-chemical solubilization techniques such as micellar solubilization by means of surface-active agents (i.e., the use of surfactant micelles to solubilize and transport the therapeutic agent). In aqueous solution, micelles can incorporate lipophilic therapeutic agents in the hydrocarbon core of the micelle, or can entangle the agents at various positions within the micelle walls. Although micellar formulations can solubilize a variety of lipophilic therapeutic agents, the loading capacity of conventional micelle formulations is limited by the solubility of the therapeutic agent in the micelle surfactant. For many lipophilic therapeutic agents, such solubility is too low to offer formulations that can deliver therapeutically effective doses.

Another method consists of preparing a derivative or an analog of the lipophilic compound having a better solubility in water than the original compound. For example, this derivative may be a water-soluble salt of the compound that usually retains the original biological activity. However, this approach is applicable only to compounds having acidic or basic properties. If more substantial modifications are introduced into the original compound to improve its solubility, a decrease or even a complete loss of the original bioactivity of the compound is frequently observed.

Another approach consists of preparing a water-soluble pro-drug capable of liberating the original bioactive compound under physiological conditions. Such pro-drugs usually improve bioavailability of the compound and can ensure a targeted delivery of the compound or its sustained release over a period of time. However, the use of pro-drugs is not universally applicable since they usually require the presence of certain functional groups in the original compound. In addition, synthetic methods of improving solubility of a compound by chemical modifications are relatively complicated and expensive.

Other methods involve the formation of complexes by the addition of chelating agents such as citric acid, tartaric acid, amino acids, thioglycolic acid, and edetate disodium. Still other methods use buffering agents such as acetate, citrate, glutamate, and phosphate salts. However, buffers and chelating agents have been implicated in imparting high levels of aluminum in products, leading to adverse side effects. Furthermore, certain chelating agents such as EDTA have been implicated in adverse events such nephrotoxicity and renal tubular necrosis.

Therefore, there is a need for improved compositions and methods for the administration of lipophilic active agents to treat a variety of disorders in subjects in need thereof.

SUMMARY

To address the foregoing problems, in whole or in part, and/or other problems that may have been observed by persons skilled in the art, the present disclosure provides compositions and methods as described by way of example as set forth below.

In one aspect, a lipophilic active agent infused food product is provided, comprising: (a) a therapeutically effective amount of a lipophilic active agent, wherein the lipophilic active agent is selected from the group consisting of a cannabinoid, nicotine, a non-steroidal anti-inflammatory drug (NSAID), and a vitamin; (b) a bioavailability enhancing agent, wherein the bioavailability enhancing agent enhances the bioavailability of the lipophilic active agent; and (c) a food product, wherein the food product is selected from the group consisting of tea leaves, coffee beans, cocoa powder, meats, fish, fruits, vegetables, dairy products, legumes, pastas, breads, grains, seeds, nuts, spices, and herbs. In another aspect, the lipophilic active agent infused food product is obtainable by the steps of: (i) contacting the food product with an oil comprising the lipophilic active agent and the bioavailability enhancing agent; and (ii) dehydrating the food product; thereby producing the lipophilic active agent infused food product. In a further aspect, step (i) comprises saturating the food product in the oil comprising the lipophilic active agent and the bioavailability enhancing agent. In yet another aspect, the lipophilic active agent infused food product further comprises a flavoring agent, particularly wherein the flavoring agent is selected from the group consisting of vanilla, vanillin, ethyl vanillin, orange oil, peppermint oil, strawberry, raspberry, and mixtures thereof. In a further aspect, the lipophilic active agent infused food product is lyophilized.

In another aspect, a lipophilic active agent infused beverage product is provided that is obtainable by the steps of: (i) providing lipophilic active agent infused tea leaves, coffee beans, or cocoa powder as described herein; and (ii) steeping the lipophilic active agent infused tea leaves, coffee beans, or cocoa powder in a liquid; thereby producing the lipophilic active agent infused beverage product.

In other aspects, a process for making a lipophilic active agent infused food product is provided comprising the steps of: (i) contacting a food product with an oil comprising a lipophilic active agent and a bioavailability enhancing agent; and (ii) dehydrating the food product; thereby producing the lipophilic active agent infused food product; wherein the lipophilic active agent infused food product comprises a therapeutically effective amount of the lipophilic active agent, and further wherein: (a) the lipophilic active agent is selected from the group consisting of a cannabinoid, nicotine, a non-steroidal anti-inflammatory drug (NSAID), and a vitamin; (b) the bioavailability enhancing agent enhances the bioavailability of the lipophilic active agent; and (c) the food product is selected from the group consisting of tea leaves, coffee beans, cocoa powder, meats, fish, fruits, vegetables, dairy products, legumes, pastas, breads, grains, seeds, nuts, spices, and herbs. In another aspect, step (i) comprises saturating the food product in the oil comprising the lipophilic active agent and the bioavailability enhancing agent. In another aspect, step (i) comprises contacting the food product with a flavoring agent, particularly wherein the flavoring agent is selected from the group consisting of vanilla, vanillin, ethyl vanillin, orange oil, peppermint oil, strawberry, raspberry, and mixtures thereof. In another aspect, the process further comprises a step of lyophilizing the lipophilic active agent infused food product. In a further aspect, wherein the lipophilic active agent infused food product is tea leaves, the process further comprises packaging the tea leaves in tea bags.

In another aspect, a process for making a lipophilic active agent infused beverage product is provided comprising making lipophilic active agent infused tea leaves, coffee beans, or cocoa powder according to any of the processes described herein; further comprising the step of steeping the lipophilic active agent infused tea leaves, coffee beans, or cocoa powder in a liquid, thereby producing the lipophilic active agent infused beverage product.

In other aspects, within the compositions and methods of the present invention, the lipophilic active agent is a cannabinoid. In another aspect, the cannabinoid is a nonpsychoactive cannabinoid such as cannabidiol.

In other aspects, within the compositions and methods of the present invention, the lipophilic active agent is an NSAID selected from the group consisting of acetylsalicylic acid, ibuprofen, acetaminophen, diclofenac, indomethacin, and piroxicam.

In other aspects, within the compositions and methods of the present invention, the lipophilic active agent is vitamin E.

In other aspects, the bioavailability enhancing agent within the compositions and methods of the present invention, the lipophilic active agent is an edible oil or fat, a protective colloid, or both a protective colloid and an edible oil or fat. In another aspect, the bioavailability enhancing agent is also a lipophilic active agent taste masking agent. In another particular aspect, where the bioavailability enhancing agent is both a protective colloid, an edible oil or fat, and a lipophilic active agent taste masking agent, the bioavailability enhancing agent is nonfat dry milk. In a further aspect, the bioavailability enhancing agent is substantially free of omega-6 fatty acids. In other aspects, the bioavailability of the lipophilic active agent in a subject is at least about 1.5 times, 2 times, 5 times, or 10 times greater than the bioavailability of the lipophilic active agent in the subject in the absence of the bioavailability enhancing agent. In a further aspect, the bioavailability of the lipophilic active agent in a subject is greater than 20%.

In a further aspect, a method of treating a condition is provided, comprising administering any of the compositions disclosed herein to a subject in need thereof. In one aspect, where the lipophilic active agent within the compositions and methods of the invention is a cannabinoid, the condition is selected from the group consisting of cardiac diseases such as heart disease, ischemic infarcts, and cardiometabolic disorders; neurological diseases such as Alzheimer's disease, Parkinson's disease, schizophrenia, and Human Immunodeficiency Virus (HIV) dementia; obesity; metabolic disorders such as insulin related deficiencies and lipid profiles, hepatic diseases, diabetes, and appetite disorders; cancer chemotherapy; benign prostatic hypertrophy; irritable bowel syndrome; biliary diseases; ovarian disorders; marijuana abuse; and alcohol, opioid, nicotine, or cocaine addiction. In another aspect, where the lipophilic active agent within the compositions and methods of the invention is nicotine, the condition is a nicotine-related disorder. In another aspect, where the lipophilic active agent within the compositions and methods of the invention is an NSAID as described herein, the condition is pain, fever, and/or an inflammatory-related disease or disorder. In another aspect, where the lipophilic active agent within the compositions and methods of the invention is a vitamin, particularly vitamin E as described herein, the condition is vitamin E deficiency and/or a vitamin E related disease or disorder.

In a further aspect, a method of enhancing the bioavailability of a lipophilic active agent is provided, comprising heating any of the compositions disclosed herein to a temperature that is greater than or equal to human body temperature. In some aspects, oral administration of any of the compositions disclosed herein to a subject in need thereof results in a heating of the compositions to a temperature that is equal to human body temperature.

Other compositions, methods, features, and advantages of the invention will be or will become apparent to one with skill in the art upon examination of the following figures and detailed description. It is intended that all such additional compositions, methods, features, and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
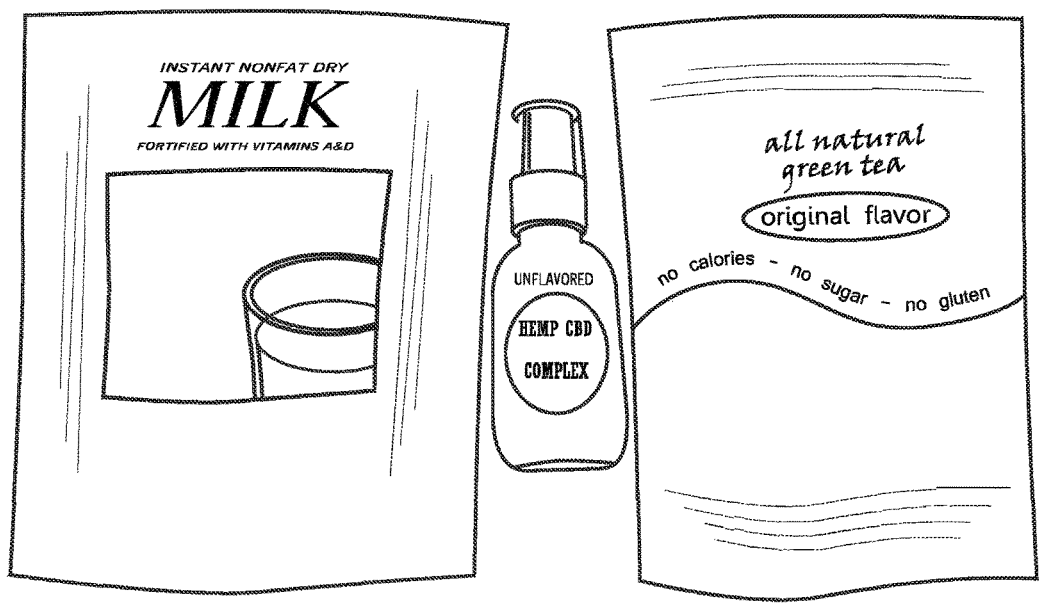
FIG. 1 is a photograph of ingredients (dry milk, tea leaves, and cannabidiol oil) used in an aspect of the present invention.

The present invention is directed to lipophilic active agent infused food and beverage compositions that provide enhanced bioavailability in a subject, particularly wherein the unpleasant taste of the lipophilic active agent is masked. Processes for making the food and beverage compositions are also provided, as well as methods for treating conditions comprising administering any of the compositions disclosed herein to a subject in need thereof.

Bioavailability refers to the extent and rate at which the active moiety (drug or metabolite) enters systemic circulation, thereby accessing the site of action. Bioavailability for a given formulation provides an estimate of the relative fraction of the orally administered dose that is absorbed into the systemic circulation. Low bioavailability is most common with oral dosage forms of poorly water-soluble, slowly absorbed drugs. Insufficient time for absorption in the gastrointestinal tract is a common cause of low bioavailability. If the drug does not dissolve readily or cannot penetrate the epithelial membrane (e.g., if it is highly ionized and polar), time at the absorption site may be insufficient. Orally administered drugs must pass through the intestinal wall and then the portal circulation to the liver, both of which are common sites of first-pass metabolism (metabolism that occurs before a drug reaches systemic circulation). Thus, many drugs may be metabolized before adequate plasma concentrations are reached.

Bioavailability is usually assessed by determining the area under the plasma concentration-time curve (AUC). AUC is directly proportional to the total amount of unchanged drug that reaches systemic circulation. Plasma drug concentration increases with extent of absorption; the maximum (peak) plasma concentration is reached when drug elimination rate equals absorption rate. Peak time is the most widely used general index of absorption rate; the slower the absorption, the later the peak time.

The bioavailability of some drugs is increased when co-administered with food, particularly agents such as cannabinoids that are Class II drugs under the Biopharmaceutical Drug Classification System (Kelepu et al. (2013) *Acta Pharmaceutica Sinica B* 3:361-372; Amidon et al. (1995) *Pharm. Res.* 12:413-420; Charman et al. (1997) *J. Pharm. Sci.* 86:269-282; Winstanley et al. (1989) *Br. J. Clin. Pharmacol.* 28:621-628). It is the lipid component of the food that plays a key role in the absorption of lipophilic drugs and that leads to enhanced oral bioavailability (Hunt & Knox (1968) *J. Physiol.* 194:327-336; Kelepu et al. (2013) *Acta Pharmaceutica Sinica B* 3:361-372). This has been attributed to the ability of a high fat meal to stimulate biliary and pancreatic secretions, to decrease metabolism and efflux activity, to increase intestinal wall permeability, and to a prolongation of gastrointestinal tract (GIT) residence time and transport via the lymphatic system (Wagnera et al. (2001) *Adv. Drug Del. Rev.* 50:513-31; Kelepu et al. (2013) *Acta Pharmaceutica Sinica B* 3:361-372). High fat meals also elevate triglyceride-rich lipoproteins that associate with drug molecules and enhance intestinal lymphatic transport, which leads to changes in drug disposition and changes the kinetics of the pharmacological actions of poorly soluble drugs (Gershkovich et al. (2007) *Eur. J. Pharm. Sci.* 32:24-32; Kelepu et al. (2013) *Acta Pharmaceutica Sinica B* 3:361-372). However, co-administration of food with lipophilic drugs requires close control and/or monitoring of food intake when dosing such drugs, and can also be subject to problems with patient compliance (Kelepu et al. (2013) *Acta Pharmaceutica Sinica B* 3:361-372).

The present invention relates, in part, to lipophilic active agent infused food and beverage compositions that provide enhanced lipophilic active agent bioavailability in a subject. It was surprisingly found that the lipid content and colloidal properties of the lipophilic active agent infused food and beverage compositions increased the bioavailability of the lipophilic active agents in subjects as compared to typical oral ingestion of the lipophilic active agents. The lipophilic active agent infused food and beverage compositions also allow for enhanced oral bioavailability associated with the co-administration of lipophilic drugs and lipid containing foods without the dosing and compliance problems associated with administration of the lipophilic active agent in a separate formulation from the foods and beverages. In addition, lipophilic active agents are surprisingly more effectively transported through the intestinal mucosa when combined with foods and beverages that also contain antioxidants such as black tea, thereby producing a synergistic effect on lipophilic active agent absorption and bioavailability.

The present invention also relates, in part, to lipophilic active agent infused food and beverage compositions comprising one or more lipophilic active agent taste masking agents. Many lipophilic active agents have unpalatable taste profiles, which could hinder the use of orally ingested lipophilic active agents as therapeutic treatments. In particular, it was surprisingly found that dry milk used within the processes for making the lipophilic active agent infused food and beverage compositions of the invention acted as both a bioavailability enhancing agent as well as a lipophilic active agent taste masking agent.

Compositions

In one aspect, a lipophilic active agent infused food product is provided, comprising: (a) a therapeutically effective amount of a lipophilic active agent, wherein the lipophilic active agent is selected from the group consisting of a cannabinoid, nicotine, a non-steroidal anti-inflammatory drug (NSAID), and a vitamin; (b) a bioavailability enhancing agent, wherein the bioavailability enhancing agent enhances the bioavailability of the lipophilic active agent; and (c) a food product, wherein the food product is selected from the group consisting of tea leaves, coffee beans, cocoa powder, meats, fish, fruits, vegetables, dairy products, legumes, pastas, breads, grains, seeds, nuts, spices, and herbs. In another aspect, the lipophilic active agent infused food product is obtainable by the steps of: (i) contacting the food product with an oil comprising the lipophilic active agent and the bioavailability enhancing agent; and (ii) dehydrating the food product; thereby producing the lipophilic active agent infused food product. In a further aspect, step (i) comprises saturating the food product in the oil comprising the lipophilic active agent and the bioavailability enhancing agent. In yet another aspect, the lipophilic active agent infused food product further comprises a flavoring agent, particularly wherein the flavoring agent is selected from the group consisting of vanilla, vanillin, ethyl vanillin, orange oil, peppermint oil, strawberry, raspberry, and mixtures thereof. In a further aspect, the lipophilic active agent infused food product is lyophilized.

In another aspect, a lyophilic active agent infused beverage product is provided that is obtainable by the steps of: (i) providing lipophilic active agent infused tea leaves, coffee beans, or cocoa powder as described herein; and (ii) steeping the lipophilic active agent infused tea leaves, coffee beans, or cocoa powder in a liquid; thereby producing the lipophilic active agent infused beverage product.

In other aspects, the bioavailability enhancing agent within the compositions and methods of the present invention, the lipophilic active agent is an edible oil or fat, a protective colloid, or both a protective colloid and an edible oil or fat. In another aspect, the bioavailability enhancing agent is also a lipophilic active agent taste masking agent. In another particular aspect, where the bioavailability enhancing agent is both a protective colloid, an edible oil or fat, and a lipophilic active agent taste masking agent, the bioavailability enhancing agent is nonfat dry milk. In a further aspect, the bioavailability enhancing agent is substantially free of omega-6 fatty acids. In other aspects, the bioavailability of the lipophilic active agent in a subject is at least about 1.5 times, 2 times, 5 times, or 10 times greater than the bioavailability of the lipophilic active agent in the subject in the absence of the bioavailability enhancing agent. In a further aspect, the bioavailability of the lipophilic active agent in a subject is greater than 20%.

An edible oil is defined herein as an oil that is capable of undergoing de-esterification or hydrolysis in the presence of pancreatic lipase in vivo under normal physiological conditions. Specifically, digestible oils may be complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of digestible oils for use in this invention thus include: vegetable, nut, or seed oils (such as coconut oil, peanut oil, soybean oil, safflower seed oil, corn oil, olive oil, castor oil, cottonseed oil, *arachis* oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (such as fish liver oil, shark oil and mink oil).

Examples of protective colloids include polypeptides (such as gelatin, casein, and caseinate), polysaccharides (such as starch, dextrin, dextran, pectin, and gum arabic), as well as whole milk, skimmed milk, milk powder or mixtures of these. However, it is also possible to use polyvinyl alcohol, vinyl polymers, for example polyvinylpyrrolidone, (meth)acrylic acid polymers and copolymers, methylcellulose, carboxymethylcellulose, hydroxypropylcellulose and alginates. For further details, reference may be made to R. A. Morton, Fast Soluble Vitamins, Intern. Encyclopedia of Food and Nutrition, Vol. 9, Pergamon Press 1970, pages 128-131.

Oral administration constitutes the preferred route of administration for a majority of drugs. However, drugs that have an undesirable or bitter taste leads to lack of patient compliance in the case of orally administered dosage forms. In such cases, taste masking is an essential tool to improve patient compliance. Because lipophilic active agents (e.g., cannabinoids such as cannabidiol) have an undesirable taste profile, in order to improve compliance, the presently disclosed compositions also comprise one or more lipophilic active agent taste masking agents. Examples of lipophilic active agent taste-masking agents include dry milk as described above, as well as menthol, sweeteners, sodium bicarbonate, ion-exchange resins, cyclodextrin inclusion compounds, adsorbates, and the like.

In a further aspect, the bioavailability enhancing agent is substantially free of omega-6 fatty acids.

In other aspects, the bioavailability of the lipophilic active agent in a subject is at least about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, or 10 times greater than the bioavailability of the lipophilic active agent in the subject in the absence of the bioavailability enhancing agent.

In a further aspect, the bioavailability of the lipophilic active agent in a subject is greater than 20% or at least about 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or greater.

Assays and methods for measuring lipophilic active agent bioavailability are well known in the art (see, e.g., Rocci & Jusko (1983) *Comput. Programs Biomed.* 16:203-215; Shargel & Yu (1999) *Applied biopharmaceutics & pharmacokinetics* (4th ed.). New York: McGraw-Hill; Hu & Li (2011) *Oral Bioavailability: Basic Principles, Advanced Concepts, and Applications*, John Wiley & Sons Ltd.; Karschner et al. (2011) *Clinical Chemistry* 57:66-75; Ohlsson et al. (1980) *Clin. Pharmacol. Ther.* 28:409-416; Ohlsson et al. (1982) *Biomed. Environ. Mass Spectrom.* 9:6-10; Ohlsson et al. (1986) *Biomed. Environ. Mass Spectrom.* 13:77-83; Karschner et al. (2010) *Anal. Bioanal. Chem.* 397:603-611).

In a further aspect, the lipophilic active agent infused food product of the present invention is lyophilized. Lyophilization, also known as freeze-drying, is a process whereby water is sublimed from a composition after it is frozen. The frozen solution is then typically subjected to a primary drying step in which the temperature is gradually raised under vacuum in a drying chamber to remove most of the water, and then to a secondary drying step typically at a higher temperature than employed in the primary drying step to remove the residual moisture in the lyophilized composition. The lyophilized composition is then appropriately sealed and stored for later use. Tang et al. (2004) *Pharmaceutical Research* 21:191-200 describes the scientific principles pertaining to freeze drying and guidelines for designing suitable freeze drying processes. Further description of freeze drying is found in Remington (2006) The Science and Practice of Pharmacy, $21^{st}$ edition, Lippincott Williams & Wilkins, pp. 828-831.

In other aspects, the compositions of the present invention further comprise a flavoring agent. Suitable flavoring agents include, but are not limited to, vanilla, vanillin, ethyl vanillin, orange oil, peppermint oil, strawberry, raspberry, and mixtures thereof.

The active agents of the present invention are effective over a wide dosage range. For example, in treating adult humans, compositions and methods of the present invention comprise dosages of lipophilic active agents from 0.01 mg to 1,000 mg, from 0.5 mg to 500 mg, from 1 mg to 100 mg, from 5 mg to 50 mg, and from 10 mg to 25 mg. Alternatively, in treating adult humans, compositions and methods of the present invention comprise dosages of lipophilic active agents of 0.01 mg, 0.05 mg, 0.1 mg, 0.25 mg, 0.5 mg, 0.75 mg, 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1,000 mg.

Cannabinoids

*Cannabis sativa* L. is one of the most widely used plants for both recreational and medicinal purposes. Over 500 natural constituents have been isolated and identified from *C. sativa* covering several chemical classes (Ahmed et al. (2008) *J. Nat. Prod.* 71:536-542; Ahmed et al. (2008)

Tetrahedron Lett. 49:6050-6053; ElSohly & Slade (2005) Life Sci. 78:539-548; Radwan et al. (2009) J. Nat. Prod. 72:906-911; Radwan et al. (2008) Planta Medial. 74:267-272; Radwan et al. (2008) J. Nat. Prod. 69:2627-2633; Ross et al. (1995) Zagazig J. Pharm. Sci. 4:1-10; Turner et al. (1980) J. Nat. Prod. 43:169-170). Cannabinoids belong to the chemical class of terpenophenolics, of which at least 85 have been uniquely identified in *cannabis* (Borgelt et al. (2013) *Pharmacotherapy* 33:195-209).

Cannabinoids are ligands to cannabinoid receptors ($CB_1$, $CB_2$) found in the human body (Pertwee (1997) *Pharmacol. Ther.* 74:129-180). The cannabinoids are usually divided into the following groups: classical cannabinoids; non-classical cannabinoids; aminoalkylindole-derivatives; and eicosanoids (Pertwee (1997) *Pharmacol. Ther.* 74:129-180). Classical cannabinoids are those that have been isolated from *C. sativa* L. or their synthetic analogs. Non-classical cannabinoids are bi- or tri-cyclic analogs of tetrahydrocannabinol (THC) (without the pyran ring). Aminoalkylindoles and eicosanoids are substantially different in structure compared to classical and non-classical cannabinoids. The most common natural plant cannabinoids (phytocannabinoids) are cannabidiol (CBD), cannabigerol (CBG), cannabichromene (CBC), and cannabinol (CBN). The most psychoactive cannabinoid is $\Delta^9$-THC.

In recent years, marijuana and its components have been reported in scientific literature to counter the symptoms of a broad range of conditions including but not limited to multiple sclerosis and other forms of muscular spasm; movement disorders; pain, including migraine headache; glaucoma; asthma; inflammation; insomnia; and high blood pressure. There may also be utility for cannabinoids as anxiolytics, anti-convulsives, anti-depressants, anti-psychotics, anti-cancer agents, as well as appetite stimulants. Pharmacological and toxicological studies of cannabinoids have largely been focused on a synthetic analog of $\Delta^9$-THC (commercially available under the generic name Dronabinol). In 1985, Dronabinol was approved by the FDA for the treatment of chemotherapy associated nausea and vomiting, and later for AIDS-associated wasting and anorexia.

Therapeutic use of cannabinoids has been hampered by the psychoactive properties of some compounds (e.g., Dronabinol) as well as their low bioavailability when administered orally. Bioavailability refers to the extent and rate at which the active moiety (drug or metabolite) enters systemic circulation, thereby accessing the site of action. The low bioavailability of orally ingested cannabinoids (from about 6% to 20%; Adams & Martin (1996) *Addiction* 91: 1585-614; Agurell et al. (1986) *Pharmacol. Rev.* 38: 21-43; Grotenhermen (2003) *Clin. Pharmacokinet.* 42: 327-60) has been attributed to their poor dissolution properties and extensive first pass metabolism.

Cannabinoids are a heteromorphic group of chemicals which directly or indirectly activate the body's cannabinoid receptors. There are three main types of cannabinoids: herbal cannabinoids that occur uniquely in the *cannabis* plant, synthetic cannabinoids that are manufactured, and endogenous cannabinoids that are produced in vivo. Herbal cannabinoids are nearly insoluble in water but soluble in lipids, alcohol, and non-polar organic solvents. These natural cannabinoids are concentrated in a viscous resin that is produced in glandular structures known as trichomes. In addition to cannabinoids, the resin is rich in terpenes, which are largely responsible for the odor of the *cannabis* plant.

The identification of $\Delta^9$-tetrahydrocannabinol (THC) as a major psychoactive drug and its chemical synthesis in 1964 opened a new era of synthetic cannabinoids as pharmacological agents. Cannabinoid research has increased tremendously in recent years since the discovery of cannabinoid receptors and the endogenous ligands for these receptors. The receptors include CB1, predominantly expressed in the brain, and CB2, primarily found on the cells of the immune system. Cannabinoid receptors belong to a superfamily of G-protein-coupled receptors. They are single polypeptides with seven transmembrane $\alpha$-helices, and have an extracellular, glycosylated N-terminus and intracellular C-terminus. Both CB1 and CB2 cannabinoid receptors are linked to G1/0-proteins. In addition to these receptors, endogenous ligands for these receptors capable of mimicking the pharmacological actions of THC have also been discovered. Such ligands were designated endocannabinoids and included anandamide and 2-arachidonoyl glycerol (2-AG). Anandamide is produced in the brain and peripheral immune tissues such as the spleen.

Unlike THC, which exerts its action by binding to CB1 and CB2, cannabidiol does not bind to these receptors and hence has no psychotropic activity. Instead, cannabidiol indirectly stimulates endogenous cannabinoid signaling by suppressing the enzyme that breaks down anandamide (fatty acid amide hydroxylase, "FAAH"). Cannabidiol also stimulates the release of 2-AG. Cannabidiol has been reported to have immunomodulating and anti-inflammatory properties, to exhibit anticonvulsive, anti-anxiety, and antipsychotic activity, and to function as an efficient neuroprotective antioxidant.

Cannabinoids in *cannabis* are often inhaled via smoking, but may also be ingested. Smoked or inhaled cannabinoids have reported bioavailabilities ranging from 2-56%, with an average of about 30% (Huestis (2007) *Chem. Biodivers.* 4:1770-1804; McGilveray (2005) *Pain Res. Manag.* 10 Suppl. A:15A-22A). This variability is mainly due to differences in smoking dynamics. Cannabinoids that are absorbed through the mucous membranes in the mouth (buccomucosal application) have bioavailabilities of around 13% (Karschner et al. (2011) *Clin. Chem.* 57:66-75). By contrast, when cannabinoids are ingested, bioavailability is typically reduced to about 6% (Karschner et al. (2011) *Clin. Chem.* 57:66-75).

Accordingly, in other aspects, within the compositions and methods of the present invention, the lipophilic active agent is a cannabinoid.

In particular aspects, at least one cannabinoid within the compositions and methods of the present invention is selected from the group consisting of:

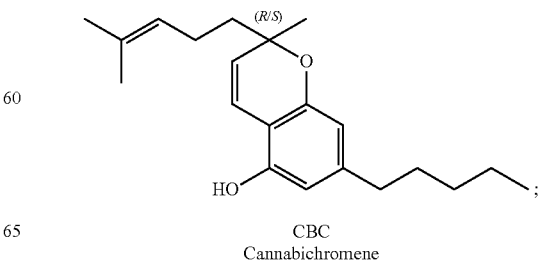

CBC
Cannabichromene

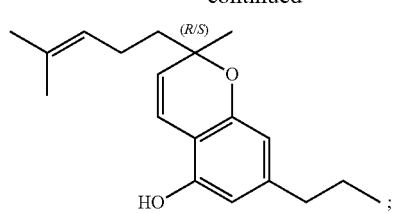
CBCV
Cannabichromenic acid
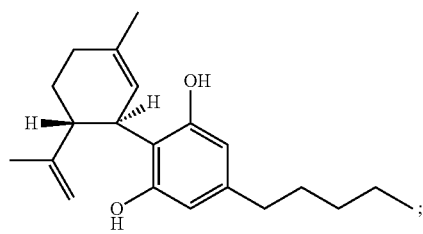
CBD
Cannabidiol
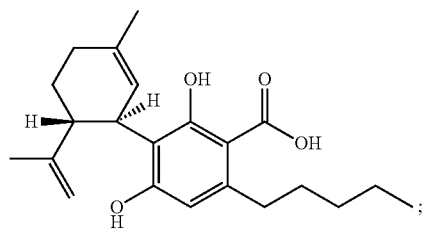
CBDA
Cannabidiolic acid
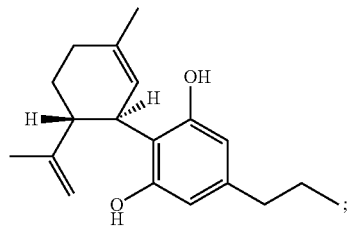
CBDV
Cannabidivarin
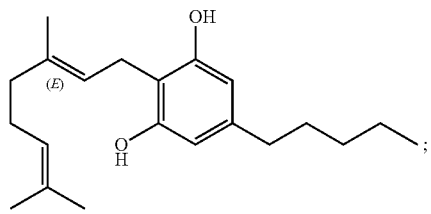
CBG
Cannabigerol
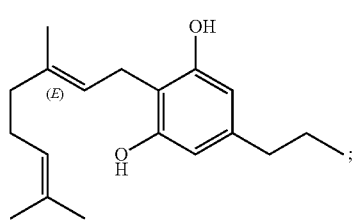
CBGV
Cannabigerol propyl variant
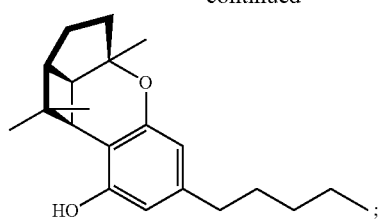
CBL
Cannabicyclol
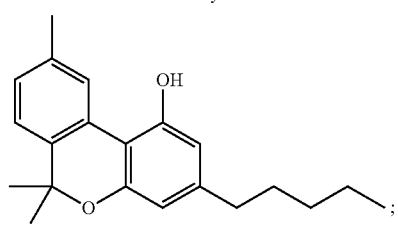
CBN
Cannabinol
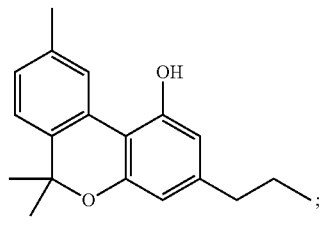
CBNV
Cannabinol propyl variant
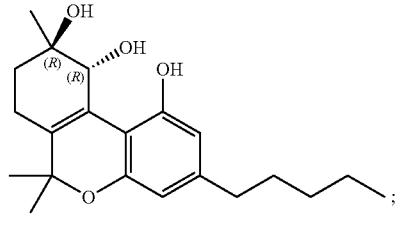
CBO
Cannabitriol
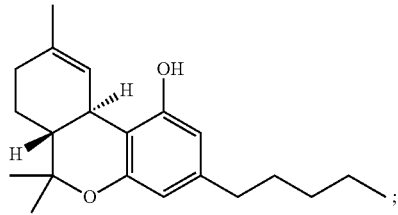
THC
Tetrahydrocannabinol
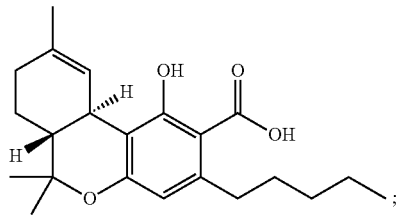
THCA
Tetrahydrocannabinolic acid

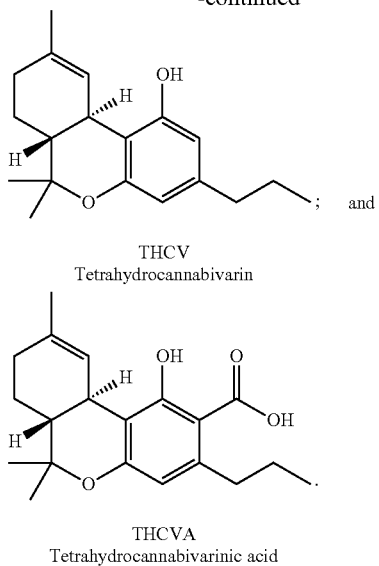

THCV
Tetrahydrocannabivarin

THCVA
Tetrahydrocannabivarinic acid

In particular aspects, at least one cannabinoid within the compositions and methods of the present invention is a non-psychoactive cannabinoid such as cannabidiol. In some particularly disclosed aspects, the cannabinoid is selected from the group consisting of:

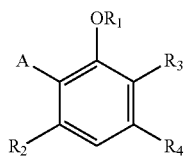

where A is aryl, and particularly

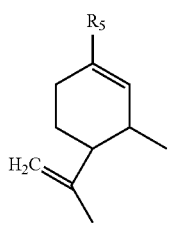

but not a pinene such as:

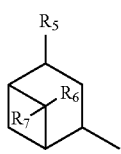

and the $R_1$-$R_5$ groups are each independently selected from the groups of hydrogen, lower substituted or unsubstituted alkyl, substituted or unsubstituted carboxyl, substituted or unsubstituted alkoxy, substituted or unsubstituted alcohol, and substituted or unsubstituted ethers, and $R_6$-$R_7$ are H or methyl. In particular aspects, there are no nitrogens in the rings, and/or no amino substitutions on the rings.

In other aspects, the cannabinoid is selected from the group consisting of:

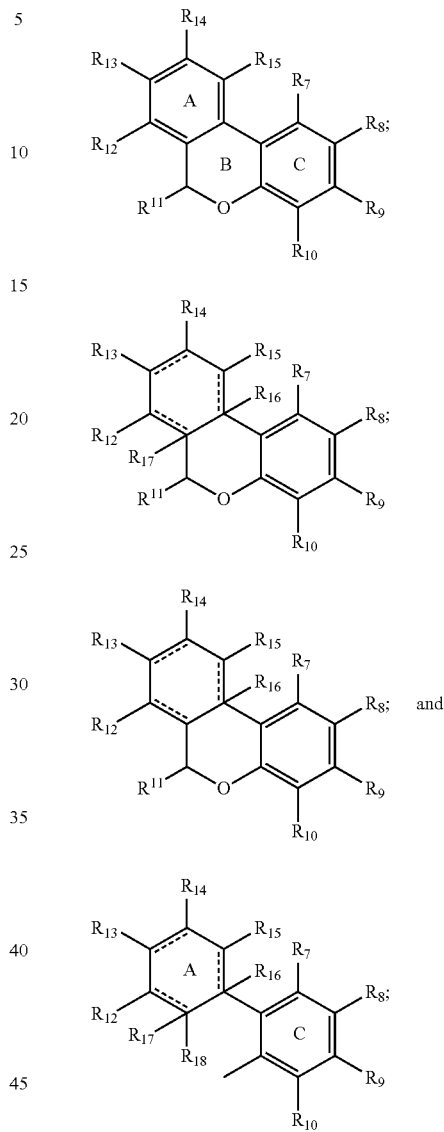

where there can be 0 to 3 double bonds on the A ring, as indicated by the optional double bonds indicated by dashed lines on the A ring. The C ring is aromatic, and the B ring can be a pyran. Particular aspects are dibenzo pyrans and cyclohexenyl benzenediols. Particular aspects of the cannabinoids of the present invention may also be highly lipid soluble, and in particular aspects can be dissolved in an aqueous solution only sparingly (for example 10 mg/ml or less). The octanol/water partition ratio at neutral pH in useful aspects is 5000 or greater, for example 6000 or greater. This high lipid solubility enhances penetration of the drug into the central nervous system (CNS), as reflected by its volume of distribution (Va.) of 1.5 L/kg or more, for example 3.5 L/kg, 7 L/kg, or ideally 10 L/kg or more, for example at least 20 L/kg. Particular aspects may also be highly water soluble derivatives that are able to penetrate the CNS, for example carboxyl derivatives.

$R_{7-18}$ are independently selected from the group of H, substituted or unsubstituted alkyl, especially lower alkyl, for example unsubstituted $C_1$-$C_3$ alkyl, hydroxyl, alkoxy, especially lower alkoxy such as methoxy or ethoxy, substituted or unsubstituted alcohol, and unsubstituted or substituted carboxyl, for example COOH or $COCH_3$. In other aspects $R_{7-18}$ can also be substituted or unsubstituted amino, and halogen.

In particular aspects, at least one cannabinoid within the compositions and methods of the present invention is a non-psychoactive cannabinoid, meaning that the cannabinoid has substantially no psychoactive activity mediated by the cannabinoid receptor (for example an $IC_{50}$ at the cannabinoid receptor of greater than or equal to 300 nM, for example greater than 1 μM and a $K_i$ greater than 250 nM, especially 500-1000 nM, for example greater than 1000 nM).

In other particular aspects, the cannabinoids within the compositions and methods of the present invention are selected from the group consisting of:

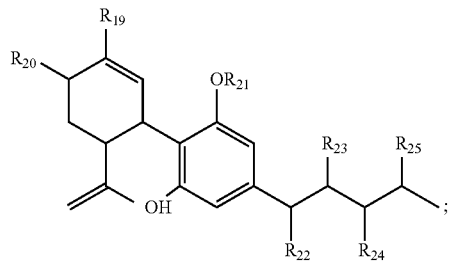

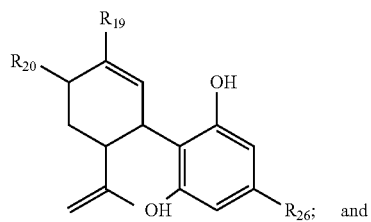

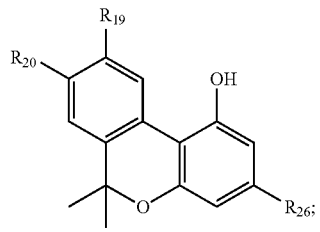

where $R_{19}$ is substituted or unsubstituted alkyl, such as lower alkyl (for example methyl), lower alcohol (such as methyl alcohol) or carboxyl (such as carboxylic acid) and oxygen (as in =O); $R_{20}$ is hydrogen or hydroxy; $R_{21}$ is hydrogen, hydroxy, or methoxy; $R_{22}$ is hydrogen or hydroxy; $R_{23}$ is hydrogen or hydroxy; $R_{24}$ is hydrogen or hydroxy; $R_{25}$ is hydrogen or hydroxy; and $R_{26}$ is substituted or unsubstituted alkyl (for example n-methyl alkyl), substituted or unsubstituted alcohol, or substituted or unsubstituted carboxy.

In other particular aspects, the cannabinoids within the compositions and methods of the present invention are selected from the group consisting of:

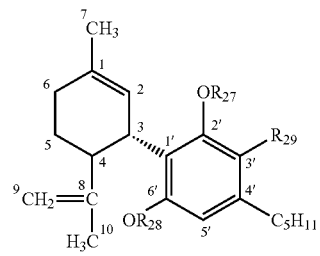

wherein numbering conventions for each of the ring positions are shown, and $R_{27}$, $R_{28}$ and $R_{29}$ are independently selected from the group consisting of H, unsubstituted lower alkyl such as $CH_3$, and carboxyl such as $COCH_3$. Particular examples of nonpsychoactive cannabinoids that fall within this definition are cannabidiol and

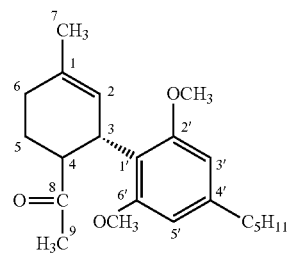

and other structural analogs of cannabidiol.

In other particular aspects, the cannabinoids within the compositions and methods of the present invention are selected from the group consisting of:

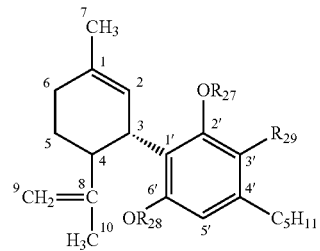

wherein $R_{27}$, $R_{28}$ and $R_{29}$ are independently selected from the group consisting of H, lower alkyl such as $CH_3$, and carboxyl such as $COCH_3$, and particularly wherein:
a) $R_{27}=R_{28}=R_{29}=H$
b) $R_{27}=R_{29}=H$; $R_{28}=CH_3$
c) $R_{27}=R_{28}=CH_3$, $R_{29}=H$
d) $R_{27}=R_{28}=COCH_3$; $R_{29}=H$
e) $R_{27}=H$; $R_{28}=R_{29}=COCH_3$ When $R_{27}=R_{28}=R_{29}=H$, then the compound is cannabidiol (CBD). When $R_{27}=R_{29}=H$ and $R_{28}=CH_3$, the compound is CBD monomethyl ether. When $R_{27}=R_{28}=CH_3$ and $R_{29}=H$, the compound is CBD dimethyl ether. When $R_{27}=R_{28}=COCH_3$ and $R_{29}=H$, the compound is CBD diacetate. When $R_{27}=H$ and $R_{28}=R_{29}=COCH_3$, the compound is CBD monoacetate.

In yet another aspect, cannabinoid infused tea leaves are packaged in tea bags, wherein each tea bag comprises 1 to 3 grams of tea leaves (dry weight), 0.10 to 1.0 grams of dry milk, and 10 to 25 mg of cannabinoid oil. In still another aspect, the cannabinoid infused tea leaves are packaged in tea bags, wherein each tea bag comprises 1.5 to 12 grams of tea leaves (dry weight), 0.10 to 6.0 grams of dry milk, 10 to 25 mg of hemp oil, and 1.0 to 12.0 grams of *cannabis* leaves.

Nicotine

More than 99% of all nicotine that is consumed worldwide is delivered through smoking cigarettes. Approximately 6,000,000 deaths per year, worldwide, are attributed primarily to the delivery of nicotine through the act of smoking according to the Centers for Disease Control and Prevention, which also estimates that over $170 billion per year is spent just in the U.S. on direct medical care costs for adult smokers. In any twelve month period, 69% of U.S. adult smokers want to quit smoking and 43% of U.S. adult smokers have attempted to quit.

Worldwide, retail cigarette sales were worth $722 billion in 2013, with over 5.7 trillion cigarettes sold to more than 1 billion smokers.

The delivery of nicotine to satisfy current demand via the compositions and methods of the present invention (i.e., in common food groups), will alleviate the consumer demand for cigarettes. Since most of the adverse health outcomes of nicotine consumption are associated with the delivery method and only to a lesser degree to the actual ingestion of nicotine, a vast positive community health outcome can be achieved through the reduction in smoking cigarettes.

Accordingly, in other aspects, within the compositions and methods of the present invention, the lipophilic active agent is nicotine.

Non-Steroidal Anti-Inflammatory Drugs (NSAIDs)

NSAIDs are the second-largest category of pain management treatment options in the world. The global pain management market was estimated at $22 billion in 2011, with $5.4 billion of this market being served by NSAID's. The U.S. makes up over one-half of the global market. The opioids market (such as morphine) form the largest single pain management sector but are known to be associated with serious dependence and tolerance issues.

Although NSAIDs are generally a safe and effective treatment method for pain, they have been associated with a number of gastrointestinal problems including dyspepsia and gastric bleeding.

Delivery of NSAIDs through the compositions and methods of the present invention will provide the beneficial properties of pain relief with lessened negative gastrointestinal effects, and also deliver lower dosages of active ingredients with similar pain management outcomes as current pill forms at higher dosages.

Accordingly, in other aspects, within the compositions and methods of the present invention, the lipophilic active agent is an NSAID, particularly wherein the NSAID is selected from the group consisting of acetylsalicylic acid, ibuprofen, acetaminophen, diclofenac, indomethacin, and piroxicam.

Vitamins

The global vitamin and supplement market is worth $68 billion according to Euromonitor. The category is both broad and deep, comprised of many popular and some lesser known substances. Vitamins in general are thought to be an $8.5 billion annual market in the U.S. The U.S. is the largest single national market in the world, and China and Japan are the $2^{nd}$ and $3^{rd}$ largest vitamin markets.

Vitamin E is fat soluble and can be incorporated into cell membranes which can protect them from oxidative damage. Global consumption of natural source vitamin E was 10,900 metric tons in 2013 worth $611.9 million.

Delivery of fat soluble vitamins through the compositions and methods of the present invention will result in less waste and lower dosages required than current pill forms. In addition, ingestion of pills is an unpleasant experience for many people so vitamin delivery through common food groups will vastly expand demand and use.

Accordingly, in other aspects, within the compositions and methods of the present invention, the lipophilic active agent is a vitamin, particularly wherein the vitamin is vitamin E.

Processes

In other aspects, a process for making a lipophilic active agent infused food product is provided comprising the steps of: (i) contacting a food product with an oil comprising a lipophilic active agent and a bioavailability enhancing agent; and (ii) dehydrating the food product; thereby producing the lipophilic active agent infused food product; wherein the lipophilic active agent infused food product comprises a therapeutically effective amount of the lipophilic active agent, and further wherein: (a) the lipophilic active agent is selected from the group consisting of a cannabinoid, nicotine, a non-steroidal anti-inflammatory drug (NSAID), and a vitamin; (b) the bioavailability enhancing agent enhances the bioavailability of the lipophilic active agent; and (c) the food product is selected from the group consisting of tea leaves, coffee beans, cocoa powder, meats, fish, fruits, vegetables, dairy products, legumes, pastas, breads, grains, seeds, nuts, spices, and herbs. In another aspect, step (i) comprises saturating the food product in the oil comprising the lipophilic active agent and the bioavailability enhancing agent. In another aspect, step (i) comprises contacting the food product with a flavoring agent, particularly wherein the flavoring agent is selected from the group consisting of vanilla, vanillin, ethyl vanillin, orange oil, peppermint oil, strawberry, raspberry, and mixtures thereof. In another aspect, the process further comprises a step of lyophilizing the lipophilic active agent infused food product.

In a further aspect, where the lipophilic active agent infused food product is tea leaves, coffee beans, or cocoa powder, the process further comprises packaging the lipophilic active agent infused tea leaves, coffee beans, or cocoa powder in single or multiple serve delivery devices, such as tea bags, water permeable membranes, pre-packaged beverage pods such as K-CUP® packs manufactured and sold by Keurig Inc. of Wakefield, Mass., and the like. Examples include, but are not limited to, such delivery devices and related systems as described in U.S. Pat. Nos. 3,450,024; 5,325,765; 5,840,189; and 6,606,938.

In another aspect, a process for making a lipophilic active agent infused beverage product is provided comprising making lipophilic active agent infused tea leaves, coffee beans, or cocoa powder according to any of the processes described herein; further comprising the step of steeping the lipophilic active agent infused tea leaves, coffee beans, or cocoa powder in a liquid, thereby producing the lipophilic active agent infused beverage product.

Methods of Treatment

In a further aspect, a method of treating a condition is provided, comprising administering any of the compositions disclosed herein to a subject in need thereof.

In one aspect, where the lipophilic active agent within the compositions and methods of the invention is a cannabinoid, the condition is selected from the group consisting of cardiac diseases such as heart disease, ischemic infarcts, and cardiometabolic disorders; neurological diseases such as Alzheimer's disease, Parkinson's disease, schizophrenia, and Human Immunodeficiency Virus (HIV) dementia; obesity; metabolic disorders such as insulin related deficiencies and lipid profiles, hepatic diseases, diabetes, and appetite disorders; cancer chemotherapy; benign prostatic hypertrophy; irritable bowel syndrome; biliary diseases; ovarian disorders; marijuana abuse; and alcohol, opioid, nicotine, or cocaine addiction.

In another aspect, where the lipophilic active agent within the compositions and methods of the invention is nicotine, the condition is a nicotine-related disorder such as tobacco dependence/addiction, Parkinson's disease, ulcerative colitis, Alzheimer's disease, schizophrenia, Attention Deficit Hyperactivity Disorder (ADHD), Tourette's syndrome, ulcerous colitis, and post-smoking-cessation weight control.

In another aspect, where the lipophilic active agent within the compositions and methods of the invention is an NSAID as described herein, the condition is pain, fever, and/or an inflammatory-related disease or disorder, including but not limited to asthma, chronic obstructive pulmonary disease, pulmonary fibrosis, inflammatory bowel disease, irritable bowel syndrome, inflammatory pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, coronary heart disease, sarcoidosis and any other disease with an inflammatory component.

In another aspect, where the lipophilic active agent within the compositions and methods of the invention is a vitamin, the condition is a vitamin deficiency or condition associated with the lipophilic vitamin. In a particular aspect, where the vitamin is vitamin E as described herein, the condition is vitamin E deficiency and/or a vitamin E related disease or disorder such as ataxia associated with vitamin E deficiency.

In a further aspect, a method of enhancing the bioavailability of a lipophilic active agent is provided, comprising heating any of the compositions disclosed herein to a temperature that is greater than or equal to human body temperature. In some aspects, oral administration of any of the compositions disclosed herein to a subject in need thereof results in a heating of the compositions to a temperature that is equal to human body temperature.

In another aspect, a method of administering any of the lipophilic active agents described herein to a subject is provided, comprising oral administration of any of the compositions of the present invention. Such administration may be for any purpose, including overall health and wellness, mental acuity, alertness, recreation, and the like.

As used herein, the term "subject" treated by the presently disclosed methods in their many aspects is desirably a human subject, although it is to be understood that the methods described herein are effective with respect to all vertebrate species, which are intended to be included in the term "subject." Accordingly, a "subject" can include a human subject for medical purposes, such as for the diagnosis or treatment of an existing disease, disorder, condition or the prophylactic diagnosis or treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some aspects, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition employed, the route of administration, the time of administration, the rate of excretion of the particular composition being employed, the duration of the treatment, other drugs, and/or materials used in combination with the particular composition employed, the age, sex, weight, condition, general health and prior medical history of the patient being treated, and like factors well known in the medical arts.

A physician having ordinary skill in the art can readily determine and prescribe the effective amount of the presently disclosed composition required. Accordingly, the dosage range for administration may be adjusted by the physician as necessary, as described more fully elsewhere herein.

EXAMPLES

Example 1

A line of CBD and/or THC infused tea bags coming in a variety of flavors was developed.

I. Ingredients

Figure 3:
FIG. 3 is a photograph of an ingredient (tea leaves) used in an aspect of the present invention.

Tea in leaf form, oil form, brewed form, organic and inorganic (FIGS. 1 and 3)

Figure 2:
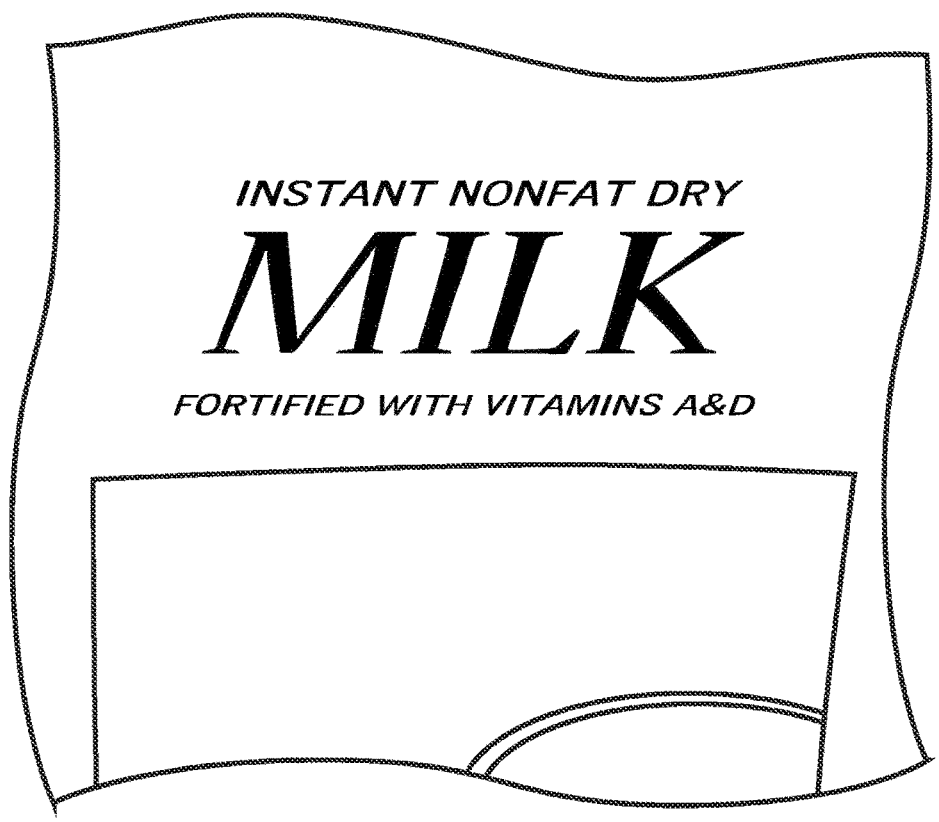
FIG. 2 is a photograph of an ingredient (dry milk) used in an aspect of the present invention.

Evaporated dry non-fat milk (FIGS. 1 and 2)

Figure 5:
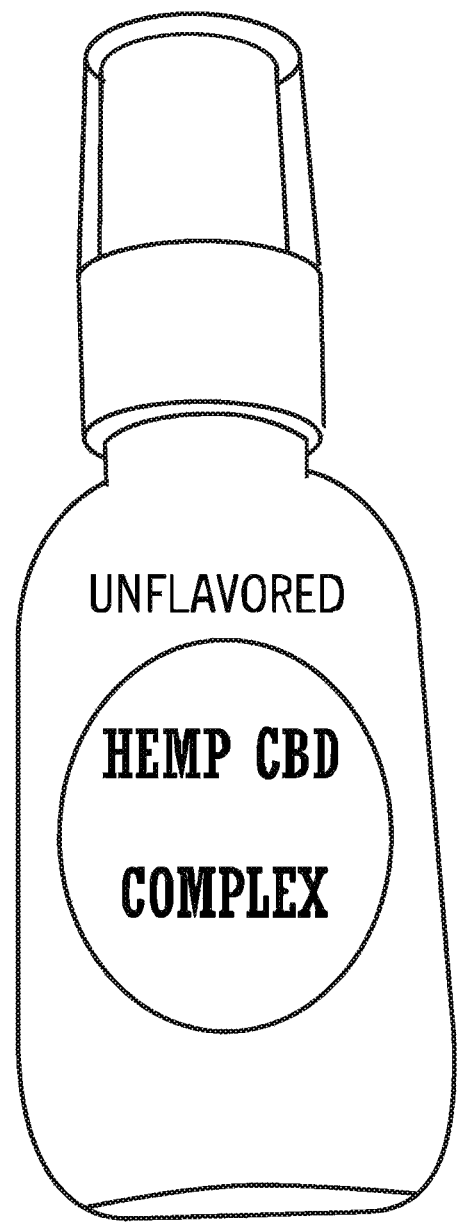
FIG. 5 is a photograph of an ingredient (cannabidiol oil) used in an aspect of the present invention.

CBD oil (FIGS. 1 and 5)

Hemp oil or compatible oil for ingestion

Cannabis leaves, buds, oils; all strains with THC and/or CBD

II. Poppy's Formulas

II A. CBD Tea

Figure 4:
FIG. 4 is a photograph of equipment (a food dehydrator) used in an aspect of the present invention.

Combine evaporated nonfat, dry milk with any and all teas, organic and inorganic Blend CBD oil with the tea leaves Dehydrate mixture of tea, CBD oil, and evaporated nonfat dry milk in a food dehydrator (FIG. 4)

Figure 6:
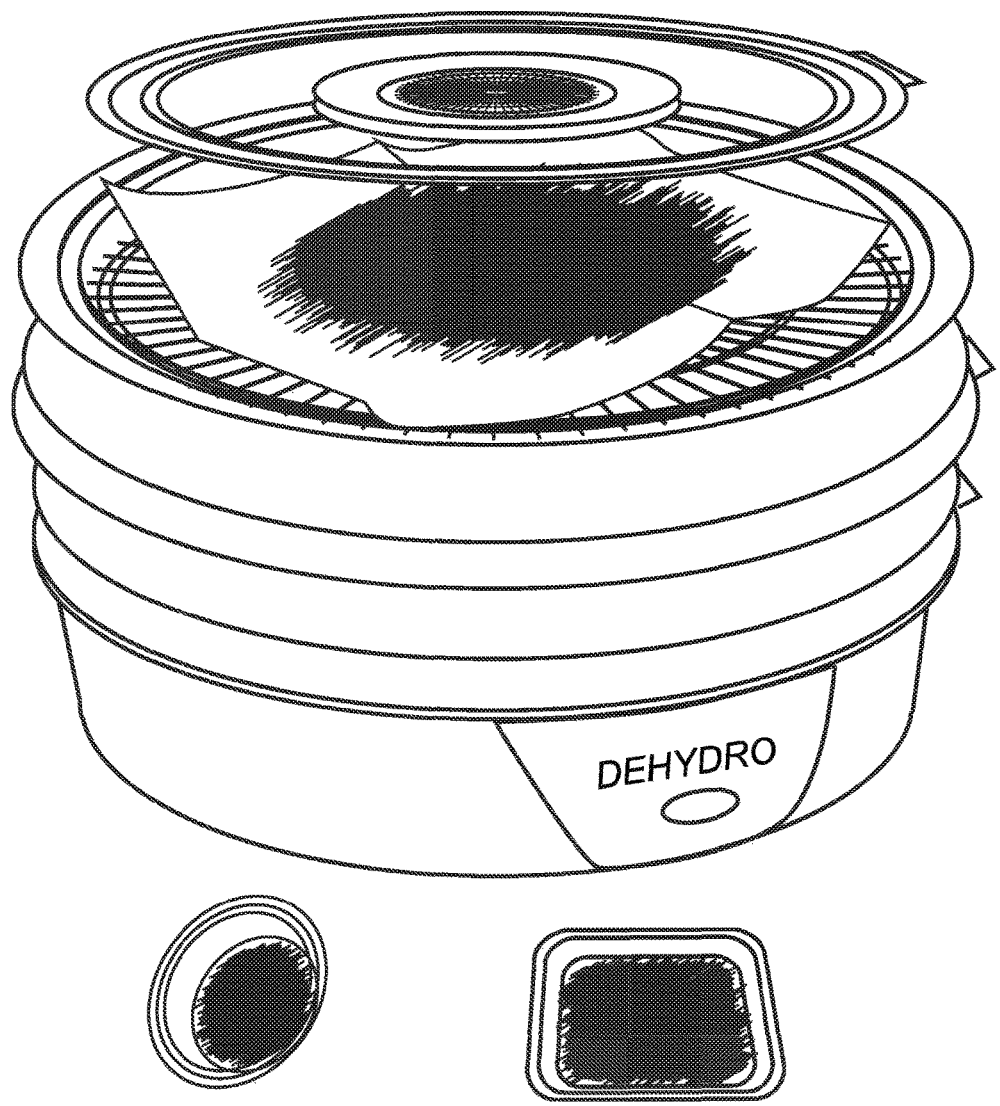
FIG. 6 is a photograph of an aspect of a composition (cannabidiol infused tea leaves) of the present invention.

End-product is Poppy's Tea with CBD enhancement only (FIG. 6)

II B. THC/CBD Tea

Combine evaporated nonfat, dry milk with any and all teas, organic and inorganic Blend hemp or other ingestible oil with the tea leaves Add cannabis leaves to above mixture Dehydrate mixture of tea, hemp or other ingestible oil, cannabis leaves, and evaporated nonfat dry milk End-product is Poppy's Tea with THC and CBD III. Poppy's Formulas: Specifications III A. CBD Tea Tea: one tea bag contains 1 gram to 3 grams of tea leaves (dry weight)

Evaporated dry non-fat milk: 0.10-1.00 grams

CBD oil: 10 mgs.-25 mgs. per tea bag

III B. THC/CBD Tea

Tea: one tea bag contains 1.5-12 grams tea leaves (dry weight) per tea bag

Evaporated dry milk: 0.10-6.00 grams per tea bag

Hemp oil or other ingestible oil: 10 mgs.-25 mgs. per tea bag

Cannabis leaves: 1.00-12.00 grams per tea bag

III C. Production Equipment:

Commercial grinder for tea and/or cannabis leaves

Commercial mixer

Commercial dehydrator

Commercial tea bag filling machine

IV. Flavorings

Poppy's Teas will provide a menu of flavorings for addition to tea bags or loose tea selections including, but not limited to mint, citrus, and vanilla.

Example 2

A process for adhering CBD and/or THC to food products was developed. The food products may be selected from the group consisting of meats, fish, fruits, vegetables, dairy products, legumes, pastas, breads, grains, seeds, nuts, spices, and herbs. The process may or may not involve contacting the food product with sunflower and/or dry evaporated milk. The process involved the steps of:

1. A food product was saturated with 0-60 grams of CBD and/or THC oil or extract.

2. The food product was placed on dehydrator paper and placed in a food dehydrator for 0-24 hours.

3. The food product was removed from the dehydrator and stored in air-tight containers.

Example 3

Black tea was formulated with various lipophilic active agents. Active agents were dosed into the tea at a concentration of approximately 4.5 mg of active ingredient per gram of finished product, using non-fat dry milk and sunflower seed oil as excipients. The following ingredients were used for the formulation:

453 g of loose leaf black tea 2265 mg active agent 45 g of instant non-fat dry evaporated milk 1132.5 mg of sunflower seed oil Ingredients were combined in a stainless steel bowl and mixed with gloved hands.

A homogenous mixture was spread evenly on a dehydrator tray and dehydrated for 30 minutes. After cooling, the formulated tea was placed into a sterile zip-lock bag.

The active ingredients that were formulated were: ASA (aspirin), ibuprofen, acetaminophen, diclofenac, indomethacin, piroxicam, nicotine, and vitamin E ($\alpha$-tocopherol). The specific supplier information and lot numbers for each active agent are shown below in Table 1.

TABLE 1

Active Agents Used for Formulations

| Compound | CAS Number | Supplier | Catalogue Number | Lot Number |
| --- | --- | --- | --- | --- |
| ASA (aspirin) | 50-78-2 | Sigma-Aldrich | A2093 | #MKBQ8444V |
| Ibuprofen | 15687-27-1 | Sigma-Aldrich | I4883 | #MKBQ4505V |
| Acetaminophen | 103-90-2 | Sigma-Aldrich | A5000 | #MKBS7142V |
| Diclofenac | 15307-79-6 | Sigma-Aldrich | D6899 | #BCBN3367V |
| Indomethacin | 53-86-1 | Sigma-Aldrich | I8280 | #MKBR4530V |
| Piroxicam | 36322-90-4 | Sigma-Aldrich | P0847 | #SLBF3478V |
| Nicotine | 54-11-5 | Sigma-Aldrich | N3876 | #1449194V |
| Vitamin E ($\alpha$-tocopherol) | 10191-41-0 | Sigma-Aldrich | 258024 | #MKBT5983V |

The Tea used was loose leaf English Breakfast Tea from Upton Tea Imports (Holliston, Mass.).

The Sunflower Oil was Whole Foods brand organic sunflower oil.

The non-fat dry milk power was NowFoods brand organic non-fat dry milk.

The dehydrator used was a Presto Dehydrator, model #06300.

Each component of the formulation was weighed out and combined as described in the above procedure. The weights of the individual active agents for each formulation are summarized below in Table 2.

TABLE 2

Formulation of Active Agents

| Compound | Compound Weight | Non-Fat Dry Milk | Sunflower Seed Oil | Black Tea | Yield | Compound Concentration |
| --- | --- | --- | --- | --- | --- | --- |
| ASA (aspirin) | 2267.1 mg | 45.09 g | 1135 mg | 453.2 g | 479.3 g | 4.52 mg/g |
| Ibuprofen | 2265.5 mg | 45.05 g | 1138 mg | 453.8 g | 488.1 g | 4.51 mg/g |
| Acetaminophen | 2264.7 mg | 45.01 g | 1136 mg | 453.2 g | 477.9 g | 4.51 mg/g |
| Diclofenac | 2265.3 mg | 45.06 g | 1133 mg | 453.1 g | 441.3 g | 4.52 mg/g |
| Indomethacin | 2266.3 mg | 44.99 g | 1138 mg | 453.1 g | 491.5 g | 4.52 mg/g |

TABLE 2-continued

Formulation of Active Agents

| Compound | Compound Weight | Non-Fat Dry Milk | Sunflower Seed Oil | Black Tea | Yield | Compound Concentration |
|---|---|---|---|---|---|---|
| Piroxicam | 2265.9 mg | 45.25 g | 1134 mg | 453.6 g | 488.3 g | 4.51 mg/g |
| Nicotine | 2264.9 mg | 45.02 g | 1133 mg | 453.1 g | 488.1 g | 4.52 mg/g |
| Vitamin E (α-tocopherol) | 2271.1 mg | 45.05 g | 1135 mg | 453.2 g | 480.2 g | 4.53 mg/g |

For each formulation, the constituents were mixed by hand until a homogeneous mixture was achieved, then spread evenly on dehydrator trays for drying. Each formulation was dried for 30 minutes in dehydrator. After cooling, mixture was placed into Zip-Lock bag. After taring the analytical balance for the Zip-Lock bag, the weight of the final formulation was recorded and the concentration of active ingredient in the formulation calculated (Table 2).

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A process for making cannabinoid infused coffee beans or cocoa powder comprising the steps of:
   (i) contacting coffee beans or cocoa powder with an oil comprising a cannabinoid and a bioavailability enhancing agent; and
   (ii) dehydrating the coffee beans or cocoa powder; thereby producing the cannabinoid infused coffee beans or cocoa powder; wherein the cannabinoid infused coffee beans or cocoa powder comprise a therapeutically effective amount of the cannabinoid, and further wherein the bioavailability enhancing agent comprises an edible oil comprising long chain fatty acids, wherein the bioavailability of the cannabinoid in a subject is at least 1.5 times greater than the bioavailability of the cannabinoid in the subject in the absence of the bioavailability enhancing agent.

2. The process for making the cannabinoid infused coffee beans or cocoa powder of claim 1, wherein the bioavailability of the cannabinoid in a subject is at least 3 times greater than the bioavailability of the cannabinoid in the subject in the absence of the bioavailability enhancing agent.

3. The process for making the cannabinoid infused coffee beans or cocoa powder of claim 1, wherein the bioavailability of the cannabinoid in a subject is at least 4.5 times greater than the bioavailability of the cannabinoid in the subject in the absence of the bioavailability enhancing agent.

4. The process for making the cannabinoid infused coffee beans or cocoa powder of claim 1, wherein the bioavailability enhancing agent is free of omega-6 fatty acids.

5. The process for making the cannabinoid infused coffee beans or cocoa powder of claim 1, wherein the cannabinoid is a psychoactive cannabinoid.

6. The process for making the cannabinoid infused coffee beans or cocoa powder of claim 1, wherein the cannabinoid is a nonpsychoactive cannabinoid.

7. The process for making the cannabinoid infused coffee beans or cocoa powder of claim 1, wherein the bioavailability enhancing agent is a protective colloid, an edible oil or fat, and a cannabinoid taste masking agent.

8. The process for making the cannabinoid infused coffee beans or cocoa powder of claim 1, wherein the bioavailability enhancing agent is nonfat dry milk.

9. The process for making the cannabinoid infused coffee beans or cocoa powder of claim 1, further wherein the cannabinoid infused coffee beans or cocoa powder are lyophilized.

10. A process for making a cannabinoid infused beverage product comprising the steps of:
    (i) contacting coffee beans or cocoa powder with an oil comprising a cannabinoid and a bioavailability enhancing agent;
    (ii) dehydrating the coffee beans or cocoa powder, thereby producing cannabinoid infused coffee beans or cocoa powder; and
    (iii) steeping the cannabinoid infused coffee beans or cocoa powder in a liquid, thereby producing the cannabinoid infused beverage product;
    wherein the cannabinoid infused coffee beans or cocoa powder comprise a therapeutically effective amount of the cannabinoid, and further wherein the bioavailability enhancing agent comprises an edible oil comprising long chain fatty acids, wherein the bioavailability of the cannabinoid in a subject is at least 1.5 times greater than the bioavailability of the cannabinoid in the subject in the absence of the bioavailability enhancing agent.

11. The process for making the cannabinoid infused beverage product of claim 10, wherein the bioavailability of the cannabinoid in a subject is at least 3 times greater than the bioavailability of the cannabinoid in the subject in the absence of the bioavailability enhancing agent.

12. The process for making the cannabinoid infused beverage product of claim 10, wherein the bioavailability of the cannabinoid in a subject is at least 4.5 times greater than the bioavailability of the cannabinoid in the subject in the absence of the bioavailability enhancing agent.

13. The process for making the cannabinoid infused beverage product of claim 10, wherein the bioavailability enhancing agent is free of omega-6 fatty acids.

14. The process for making the cannabinoid infused beverage product of claim 10, wherein the cannabinoid is a psychoactive cannabinoid.

15. The process for making the cannabinoid infused beverage product of claim 10, wherein the cannabinoid is a nonpsychoactive cannabinoid.

16. The process for making the cannabinoid infused beverage product of claim 10, wherein the bioavailability enhancing agent is a protective colloid, an edible oil or fat, and a cannabinoid taste masking agent.

17. The process for making the cannabinoid infused beverage product of claim 10, wherein the bioavailability enhancing agent is nonfat dry milk.

18. The process for making the cannabinoid infused beverage product of claim 10, further wherein the cannabinoid infused coffee beans or cocoa powder are lyophilized.

* * * * *